(12) United States Patent
Zare et al.

(10) Patent No.: US 8,289,519 B2
(45) Date of Patent: Oct. 16, 2012

(54) SURFACE PLASMON RESONANCE (SRP) MICROSCOPY SYSTEMS, METHOD OF FABRICATION THEREOF, AND METHODS OF USE THEREOF

(75) Inventors: Richard Neil Zare, Stanford, CA (US);
Yiqi Luo, Mountain View, CA (US);
Fang Yu, Mountain View, CA (US)

(73) Assignee: Stanford University, Palo Alto, CA (US)

( * ) Notice: Subject to any disclaimer, the term of this patent is extended or adjusted under 35 U.S.C. 154(b) by 1169 days.

(21) Appl. No.: 12/077,771

(22) Filed: Mar. 21, 2008

(65) Prior Publication Data

US 2012/0154814 A1    Jun. 21, 2012

Related U.S. Application Data

(60) Provisional application No. 60/919,292, filed on Mar. 21, 2007.

(51) Int. Cl.
*G01N 21/55* (2006.01)

(52) U.S. Cl. .................................................... 356/445
(58) Field of Classification Search ................... 356/445
See application file for complete search history.

(56) References Cited

U.S. PATENT DOCUMENTS

| | | | |
|---|---|---|---|
| 2007/0183934 A1* | 8/2007 | Diercks et al. | 422/100 |
| 2008/0285040 A1* | 11/2008 | Fourkas et al. | 356/445 |
| 2010/0061892 A1* | 3/2010 | Flaim et al. | 422/68.1 |

* cited by examiner

*Primary Examiner* — Kara E Geisel
(74) *Attorney, Agent, or Firm* — Thomas, Kayden, Horstemeyer & Risley, LLP

(57) ABSTRACT

Surface plasmon resonance (SPR) microscopy systems, methods of making SPR microscopy systems, methods of measuring and detecting the presence of one or more compounds present in a sample using the SPR microscopy system, and the like, are disclosed. In an embodiment, a surface plasmon resonance (SPR) microscopy system can include an integrated microfluidic chip that includes a plurality of layers, an SPR imaging system, and a pressure manifold to actuate flow control components in the integrated microfluidic chip.

16 Claims, 11 Drawing Sheets
(5 of 11 Drawing Sheet(s) Filed in Color)

SURFACE PLASMON RESONANCE (SRP) MICROSCOPY SYSTEMS, METHOD OF FABRICATION THEREOF, AND METHODS OF USE THEREOF

CROSS-REFERENCE TO RELATED APPLICATION

This application claims priority to U.S. provisional application entitled, "SURFACE PLASMON RESONANCE (SPR) MICROSCOPY SYSTEMS, METHOD OF FABRICATION THEREOF, AND METHODS OF USE THEREOF," having Ser. No. 60/919,292, filed on Mar. 21, 2007, which is entirely incorporated herein by reference.

FEDERALLY-SPONSORED RESEARCH OR DEVELOPMENT

This invention was made with Government support under contract 0411641 awarded by the National Science Foundation. The Government has certain rights in this invention.

BACKGROUND

Surface plasmon resonance (SPR) is a general spectroscopic method for sensing refractive index changes near the surface of a metal film. Its sensitivity to these changes provides a versatile platform for the observation and quantitation of chemical reactions at the metal/solution interface. SPR allows detection of small changes in refractive index that result from interactions between surface-confined molecules and solution-borne species.

SPR relies on the optical excitation of surface modes (plasmons) in a free electron metal. Back-side, p-polarized illumination of a prism-coupled film at some angle greater than the critical angle for total internal reflection results in plasmon excitation at the metal-solution interface. Plasmon excitation is observed as an increase in optical absorbance (decrease in reflectance) at an optimal coupling angle. This, in turn, results in a minimum in the SPR profile (a plot of reflectance versus angle), which is referred to as the plasmon angle. Sensing via SPR is possible due to the sensitivity of plasmon angle to changes in the index of refraction near the metal surface. Adsorption, desorption, and molecule-molecule interactions that occur at the metal-solution interface result in such changes, thereby inducing a shift in plasmon angle. These changes can be monitored in real-time, making SPR suitable for dynamic sensing.

SUMMARY

Embodiments of the present disclosure provide for surface plasmon resonance (SPR) microscopy systems, methods of making SPR microscopy systems, methods of measuring and detecting the presence of one or more compounds present in a sample using the SPR microscopy system, and the like.

One exemplary SPR microscopy system, among others, includes: an integrated microfluidic chip that includes a plurality of layers, wherein the microfluidic chip includes at least a first layer and a second layer, wherein a first layer includes a plurality of microfluidic channels, wherein a second layer includes one or more flow control components, wherein an array of metal spots is disposed on a side of the channels in the first layer, and an SPR imaging system, wherein the SPR imaging system is adapted to detect a SPR signal associated with each metal spot, and a pressure manifold to actuate flow control components in the second layer of the microfluidic chip and to realize pressure-driven flow of liquids in the channels in the first layer of the microfluidic chip.

One exemplary method of the label-free detection of a first target/second target pair, among others, includes: providing the surface plasmon resonance (SPR) microscopy system, wherein the SPR microscopy system includes: an integrated microfluidic chip that includes a plurality of layers, wherein the microfluidic chip includes a first layer and a second layer, wherein a first layer includes a plurality of microfluidic channels, wherein a second layer includes one or more flow control components, wherein an array of metal spots is disposed on a side of the channels in the first layer, wherein the plurality of microfluidic channels in the first layer of the microfluidic chip includes a first set of channels and a second set of channels, wherein the first set of channels and the second set of channels are in communication at a position where a channel of the first set of channels and a channel of the second set of channels intersect one another, and wherein a metal spot of the array of the metal spots is located at the position where each pair of perpendicular channels intersects one another, and an SPR imaging system, wherein the SPR imaging system is adapted to detect an SPR signal associated with each metal spot; exposing the array of metal spots to a sample including a second target, wherein the first target and the second target interact to form a first target/second target pair; and detecting an SPR signal associated with each metal spot, wherein detection of the SPR signal is correlated to the presence or absence of the first target/second target pair.

These embodiments, uses of these embodiments, and other uses, features and advantages of the present disclosure, will become more apparent to those of ordinary skill in the relevant art when the following detailed description of the preferred embodiments is read in conjunction with the appended figures.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

The patent or application file contains at least one drawing executed in color. Copies of this patent or patent application publication with color drawing(s) will be provided by the Office upon request and payment of the necessary fee.

FIG. 1(b) illustrates the layout of the control layer of the microfluidic chip. FIG. 1(c) illustrates the layout of the channel layer of the microfluidic chip. FIG. 1(d) illustrates the layout of the substrate of the microfluidic chip having a layer of metal spots deposited on certain areas of the substrate. FIG. 1(e) illustrates the layout of the assembled microfluidic chip, i.e. FIGS. 1(b)+1(c)+1(d). The valves (red and blue rectangles) in the control layer are aligned onto the channels (light and dark green lines) in the channel layer. The metal spots (brown dots) are located at the intersections of the channels. Two neighboring channels are connected to the same inlet and outlet reservoirs. This design permits four replications of each immunoreaction.

FIGS. 1(f) and 1(g) are digital images.

DETAILED DESCRIPTION

Figure 1A:
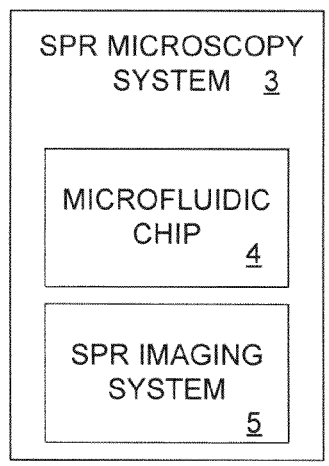
FIG. 1(a) illustrates an embodiment of a SPR microscopy system.

Embodiments of the present disclosure will employ, unless otherwise indicated, techniques of chemistry, synthetic organic chemistry, biochemistry, biology, molecular biology, and the like, which are within the skill of the art. Such techniques are explained fully in the literature.

Before the present disclosure is described in greater detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit (unless the context clearly dictates otherwise), between the upper and lower limit of that range, and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

DEFINITIONS

In describing and claiming the disclosed subject matter, the following terminology will be used in accordance with the definitions set forth below.

In accordance with the present disclosure there may be employed conventional molecular biology, microbiology, and recombinant DNA techniques within the skill of the art. Such techniques are explained fully in the literature. See, e.g., Maniatis, Fritsch & Sambrook, "Molecular Cloning: A Laboratory Manual (1982); "DNA Cloning: A Practical Approach," Volumes I and II (D. N. Glover ed. 1985); "Oligonucleotide Synthesis" (M. J. Gait ed. 1984); "Nucleic Acid Hybridization" (B. D. Hames & S. J. Higgins eds. (1985)); "Transcription and Translation" (B. D. Hames & S. J. Higgins eds. (1984)); "Animal Cell Culture" (R. I. Freshney, ed.

(1986)); "Immobilized Cells and Enzymes" (IRL Press, (1986)); B. Perbal, "A Practical Guide To Molecular Cloning" (1984), each of which is incorporated herein by reference.

As used herein, the terms "antibody" and "antibodies" can include, but are not limited to, monoclonal antibodies, multispecific antibodies, human antibodies, humanized antibodies, camelised antibodies, chimeric antibodies, single-chain Fvs (scFv), single chain antibodies, Fab fragments, F(ab') fragments, disulfide-linked Fvs (sdFv), and anti-idiotypic (anti-Id) antibodies (e.g., anti-Id antibodies to antibodies of the disclosure), and epitope-binding fragments of any of the above. In particular, antibodies include immunoglobulin molecules and immunologically active fragments of immunoglobulin molecules (e.g., molecules that contain an antigen binding site). Immunoglobulin molecules can be of any type (e.g., IgG, IgE, IgM, IgD, IgA and IgY), class (e.g., IgG1, IgG2, IgG3, IgG4, IgA1 and IgA2), or subclass. The antibodies may be from any animal origin including birds and mammals (e.g., human, murine, donkey, sheep, rabbit, goat, guinea pig, camel, horse, or chicken). Preferably, the antibodies are human or humanized monoclonal antibodies. As used herein, "human" antibodies include antibodies having the amino acid sequence of a human immunoglobulin and include antibodies isolated from human immunoglobulin libraries or from mice that express antibodies from human genes. The antibodies may be monospecific, bispecific, trispecific, or of greater multispecificity.

As used herein, "humanized" describes antibodies wherein some, most, or all of the amino acids outside the complementarity-determining regions (CDR regions) are replaced with corresponding amino acids derived from human immunoglobulin molecules. In one embodiment of the humanized forms of the antibodies, some, most, or all of the amino acids outside the CDR regions have been replaced with amino acids from human immunoglobulin molecules but where some, most, or all amino acids within one or more CDR regions are unchanged. Small additions, deletions, insertions, substitutions or modifications of amino acids are permissible as long as they would not abrogate the ability of the antibody to bind a given antigen. Suitable human immunoglobulin molecules would include IgG1, IgG2, IgG3, IgG4, IgA, and IgM molecules. A "humanized" antibody would retain a similar antigenic specificity as the original antibody.

As used herein, "antigen" describes a compound, a composition, or a substance that can stimulate the production of antibodies or a T-cell response in a host.

The term "polypeptides" includes proteins and fragments thereof. Polypeptides are disclosed herein as amino acid residue sequences. Those sequences are written left to right in the direction from the amino to the carboxy terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V).

The term "polymer" means any compound that is made up of two or more monomeric units covalently bonded to each other, where the monomeric units may be the same or different, such that the polymer may be a homopolymer or a heteropolymer. Representative polymers include peptides, polysaccharides, nucleic acids and the like, where the polymers may be naturally occurring or synthetic.

As used herein, the term "polynucleotide" generally refers to any polyribonucleotide or polydeoxribonucleotide, which may be unmodified RNA or DNA or modified RNA or DNA. Thus, for instance, polynucleotides as used herein refers to, among others, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. The terms "nucleic acid," "nucleic acid sequence," or "oligonucleotide" also encompasses a polynucleotide as defined above.

In addition, polynucleotide as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide.

As used herein, the term polynucleotide includes DNAs or RNAs as described above that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein.

It will be appreciated that a great variety of modifications have been made to DNA and RNA that serve many useful purposes known to those of skill in the art. The term polynucleotide as it is employed herein embraces such chemically, enzymatically, or metabolically modified forms of polynucleotides, as well as the chemical forms of DNA and RNA characteristic of viruses and cells, including simple and complex cells, inter alias.

"Aptamers" may be high affinity, high specificity polypeptide, RNA, or DNA-based probes produced by in vitro selection experiments. Aptamers may be generated from random sequences of nucleotides or amino acids, selectively screened by absorption to molecular antigens or cells, and enriched to purify specific high affinity binding ligands, for example. In solution, aptamers may be unstructured but may fold and enwrap target epitopes providing specific binding recognition. The unique folding of the nucleic acids around the epitope, for example, affords discriminatory intermolecular contacts through hydrogen bonding, electrostatic interaction, stacking, and shape complementarity.

Use of the phrase "biomolecule" is intended to encompass deoxyribonucleic acid (DNA), ribonucleic acid (RNA), nucleotides, oligonucleotides, nucleosides, polynucleotides, proteins, peptides, polypeptides, selenoproteins, antibodies, antigens, protein complexes, aptamers, combinations thereof, and the like.

Use of "biological" or "biological target" is intended to encompass biomolecules (e.g., deoxyribonucleic acid (DNA), ribonucleic acid (RNA), nucleotides, oligonucleotides, nucleosides, polynucleotides, proteins, peptides, polypeptides, selenoproteins, antibodies, antigens, protein complexes, aptamers, combinations thereof) and the like. In particular, biological or biological target can include, but is not limited to, naturally occurring substances such as polypeptides, polynucleotides, lipids, fatty acids, glycoproteins, carbohydrates, fatty acids, fatty esters, macromolecular polypeptide complexes, vitamins, co-factors, whole cells, eukaryotic cells, prokaryotic cells, micelles, microorganisms such as viruses, bacteria, protozoa, archaea, fungi, algae, spores, apicomplexan, trematodes, nematodes, mycoplasma, or combinations thereof. In addition, the biological target can include native intact cells, viruses, bacterium, and the like.

Use of the term "affinity" can include biological interactions and/or chemical interactions. The biological interactions can include, but are not limited to, bonding or hybridization among one or more biological functional groups located on the first biomolecule or biological target and the second biomolecule or biological target. The chemical interaction can include, but is not limited to, bonding among one or more functional groups (e.g., organic and/or inorganic functional groups) located on the biomolecules.

The term "array" encompasses the term "microarray" and refers to an ordered array presented for binding to polynucleotides and the like.

An "array" includes any two-dimensional or substantially two-dimensional (as well as a three-dimensional) arrangement of addressable regions including nucleic acids (e.g., particularly polynucleotides or synthetic mimetics thereof) and the like. Where the arrays are arrays of polynucleotides, the polynucleotides may be adsorbed, physisorbed, chemisorbed, and/or covalently attached to the arrays at any point or points along the nucleic acid chain.

A substrate may carry one, two, four or more arrays disposed on a front surface of the substrate. Depending upon the use, any or all of the arrays may be the same or different from one another and each may contain multiple spots or features. A typical array may contain one or more, including more than two, more than ten, more than one hundred, more than one thousand, more than ten thousand features, or even more than one hundred thousand features, in an area of less than about 20 $cm^2$ or even less than about 10 $cm^2$ (e.g., less than about 5 $cm^2$, including less than about 1 $cm^2$ or less than about 1 $mm^2$ (e.g., about 100 $\mu m^2$, or even smaller)). For example, features may have widths (that is, diameter, for a round spot) in the range from about 10 µm to 1.0 cm. Non-round features may have area ranges equivalent to that of circular features with the foregoing width (diameter) ranges.

Arrays can be fabricated using drop deposition from pulsejets of either polynucleotide precursor units (such as monomers), in the case of in situ fabrication, or the previously obtained nucleic acid. Such methods are described in detail, for example, in U.S. Pat. Nos. 6,242,266, 6,232,072, 6,180,351, 6,171,797, and 6,323,043. As already mentioned, these references are incorporated herein by reference.

An array "package" may be the array plus a substrate on which the array is deposited, although the package may include other features (such as a housing with a chamber). A "chamber" references an enclosed volume (although a chamber may be accessible through one or more ports). It will also be appreciated that throughout the present application, that words such as "top," "upper," and "lower" are used in a relative sense only.

An array is "addressable" when it has multiple regions of different moieties (e.g., different polynucleotide sequences) such that a region (i.e., a "feature" or "spot" of the array) at a particular predetermined location (i.e., an "address") on the array will detect a particular probe sequence. Array features are typically, but need not be, separated by intervening spaces. In the case of an array in the context of the present application, the "probe" will be referenced in certain embodiments as a moiety in a mobile phase (typically fluid), to be detected by "targets," which are bound to the substrate at the various regions.

A "scan region" refers to a contiguous (preferably, rectangular) area in which the array spots or features of interest, as defined above, are found or detected. The scan region is that portion of the total area queried from which resulting signal is detected and recorded.

An "array layout" refers to one or more characteristics of the features, such as feature positioning on the substrate, one or more feature dimensions, and an indication of a moiety at a given location.

Discussion

In accordance with the purpose(s) of the present disclosure, as embodied and broadly described herein, embodiments of the present disclosure, in one aspect, relate to surface plasmon resonance (SPR) microscopy systems, methods of making SPR microscopy systems, methods of measuring and detecting the presence of one or more compounds present in a sample using the SPR microscopy system, and the like.

The SPR microscopy system includes, but is not limited to, an integrated microfluidic chip having an array of metal spots disposed within the channels of the microfluidic chip, an SPR imaging system, and a pressure manifold to actuate flow control components and realize pressure-driven flow of liquids in the microfluidic chip. In an embodiment, the SPR microscopy system includes an integrated microfluidic chip that includes a plurality of layers. The plurality of layers is permanently attached to one another to form an intact assembly. The integrated microfluidic chip is an intact assembly that is not reassembled in use. In an embodiment, the microfluidic chip includes at least a first layer and a second layer. The first layer includes a plurality of microfluidic channels, and the second layer includes one or more flow control components (e.g., valves, pumps, valve or channel gates that can open and close, and the like). The first layer and the second layer are in communication (e.g., in one embodiment the pressure from one layer can be used to move fluid in the other layer (pressure-driven flow of liquid via pressure actuation) or in another embodiment the fluid can flow directly or indirectly from one to the other). An array of metal spots (e.g., 1 to 1024) is disposed on a substrate that define a wall or side of the channels in the first layer. In other words, the metal spots are disposed within the channels of the first layer and on one of the sides (e.g., bottom side) or walls (e.g., bottom wall) that define the channel. In another embodiment, the pressure-driven flow in the microfluidic chip can be realized not by the pressure manifold but an additional device such as peristaltic pumps, piston pumps, and combinations thereof. It should be noted that each "layer" is not necessarily a layer that has equal distance to the sensing surface. In addition, the layers are not necessarily parallel to each other.

Embodiments of the present disclosure are molecular recognition systems in that the systems can be used to detect and/or measure the interaction (e.g., chemically, biologically, biochemically, and/or physically) of a first target (e.g., chemical target, biological target, and the like) bound (e.g., chemical bonding (e.g., covalent, non-covalent, or ionic bonding), biological interaction, biochemical interaction, physical interaction, chelation interaction, hydrophobic interactions, hydrophilic interactions, charge-charge interactions, π-stacking interactions, combinations thereof, and/or otherwise associated with one another) to the surface of the metal spot with one or more targets present in a sample. The first target may interact with the target(s) present in the sample and then can be detected. The metal spots and the channels of the integrated microfluidic chip can be set up to form an array to test a plurality of concentrations so the SPR microscopy system can be a high throughput system.

In particular, the SPR microscopy system detects and/or measures the refractive index change of molecules (e.g., first target and the target from the sample (also referred to as "target-target systems")) bound to the surface of the metal spot and therefore, provides label-free detection of the target (s) of interest. Embodiments of the SPR microscopy system enable the analysis of one or more target-target systems in three dimensions, which include: signal intensity along the x- and y-axis of the array, and signal intensity as a function of time of each sensing spot (metal spot)). The type and/or concentration of the targets can be varied along the x- and y-axis position of the metal spots, while the kinetic constants and affinity information of the interaction between targets can be directly obtained from the measurements as a function of time. Additional details are described herein.

It should also be noted that the large field of view of the SPR imaging system (on the order of square centimeters) and the easy-to-use microfabrication method for the microfluidic chip (e.g., PDMS (soft lithography)) facilitates high throughput of the system.

Embodiments of the SPR microscopy system enable the rapid analysis of samples, where the amount of sample used/consumed can be very small (e.g., nanoliter volumes). In particular, embodiments of the SPR microscopy system include an integrated microfluidic chip having nanoliter volume sample loading channels and reaction chambers, which significantly enhances the speed of chemical interaction and/or bonding (e.g., antibody-antigen binding) while reducing the sample consumption. In a particular embodiment, an antibody-antigen reaction can be detected and/or measured in real-time using an embodiment of the SPR microscopy system, compared to several hours or more for standard ELISA techniques.

As mentioned above, embodiments of the SPR microscopy system can be used to detect the presence of a target, measure the amount of target present, and calculate the binding kinetic constants between targets. The first target or the target of interest in the sample can be a chemical target or a biological target. In an embodiment, the first target can be selected using appropriate recognition chemistries and/or recognition biologies for the target of interest.

The chemical target can include, but is not limited to, halogenated hydrocarbons, aromatic hydrocarbons, volatile organic compounds, surfactants, polycyclic aromatic hydrocarbons (PAHs), pesticides, macromolecules, pathogens, toxins, nerve agents, chemical/biochemical/biological warfare agents. The chemical target is not limited to those mentioned above, but rather the chemical compound can include a large number of compounds that are amenable to being detected using embodiments of the present disclosure.

The biological target can include, but is not limited to, biomolecules (e.g., deoxyribonucleic acid (DNA), ribonucleic acid (RNA), nucleotides, oligonucleotides, nucleosides, polynucleotides, proteins, peptides, polypeptides, selenoproteins, antibodies, antigens, protein complexes, aptamers, combinations thereof) and the like. In particular, the biological target can include, but is not limited to, naturally occurring substances such as polypeptides, polynucleotides, lipids, fatty acids, glycoproteins, carbohydrates, fatty acids, fatty esters, macromolecular polypeptide complexes, vitamins, co-factors, whole cells, eukaryotic cells, prokaryotic cells, micelles, microorganisms such as viruses, bacteria, protozoa, archaea, fungi, algae, spores, apicomplexan, trematodes, nematodes, mycoplasma, or combinations thereof. In addition, the biological target can include native intact cells, viruses, bacterium, and the like.

Embodiments of the present disclosure can be used in devices such as, but not limited to, point-of-care devices to detect and/or measure one or more chemical and/or biological targets in a fluid (e.g., blood, urine, etc), monitoring devices to measure targets in a fluid sample (e.g., environmental samples, etc), gas sensing system, humidity sensing system, and other sensing devices and systems applicable to the SPR microscopy system.

An embodiment of the microfluidic chip includes a network of nanoliter-scale channels that are connected to accomplish functions such as chemical and/or biochemical reactions. In another embodiment, the microfluidic chip can include channels having a larger volume for embodiments where the volume used is not a significant variable. In this regard, the dimensions of the channels can vary depending upon the use of the SPR microscopy system.

Figure 1B:
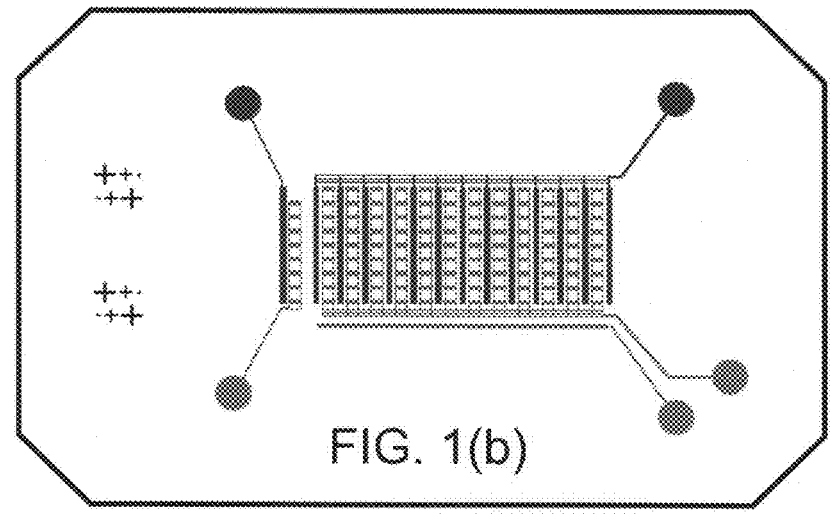
FIGS. 1(b)-1(e) illustrate an embodiment of a microfluidic chip designed for coupling with an SPR imaging system.
Figure 1C:
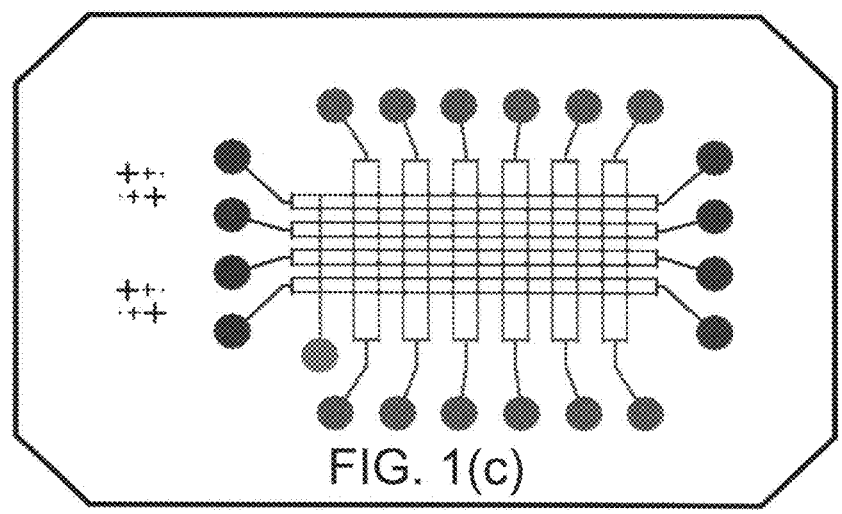
Figure 1D:
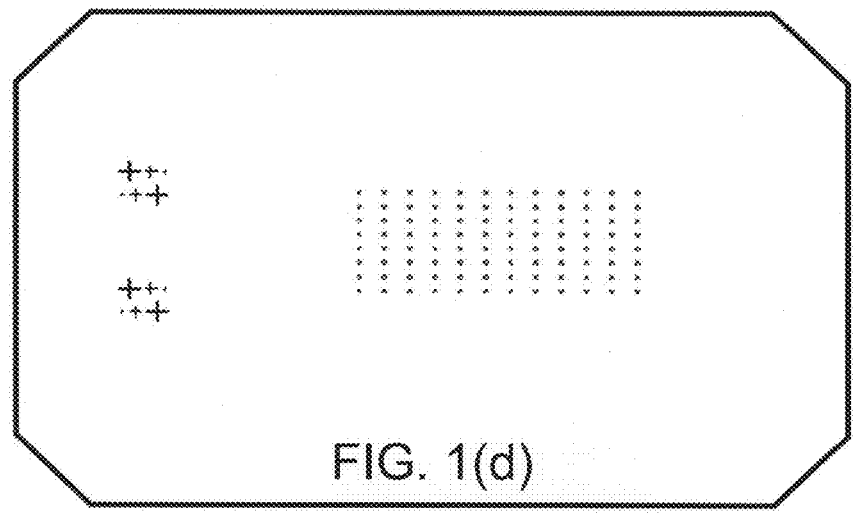
Figure 1E:
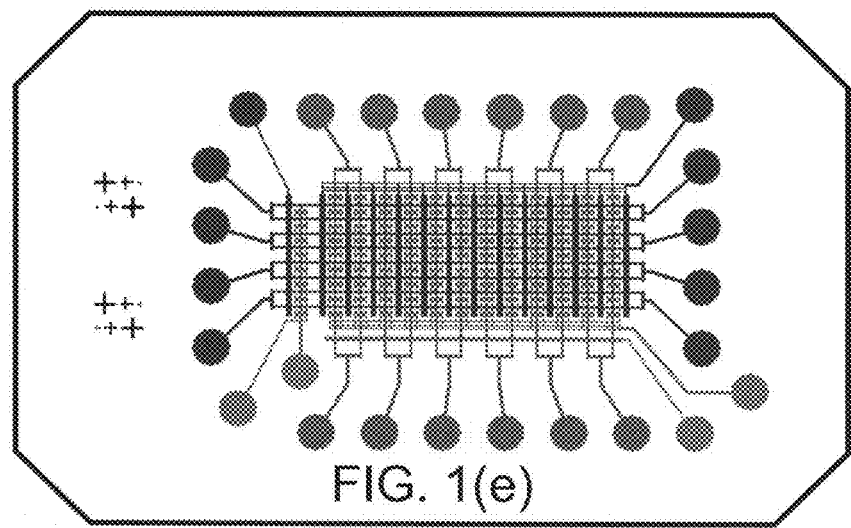
Figure 1F:
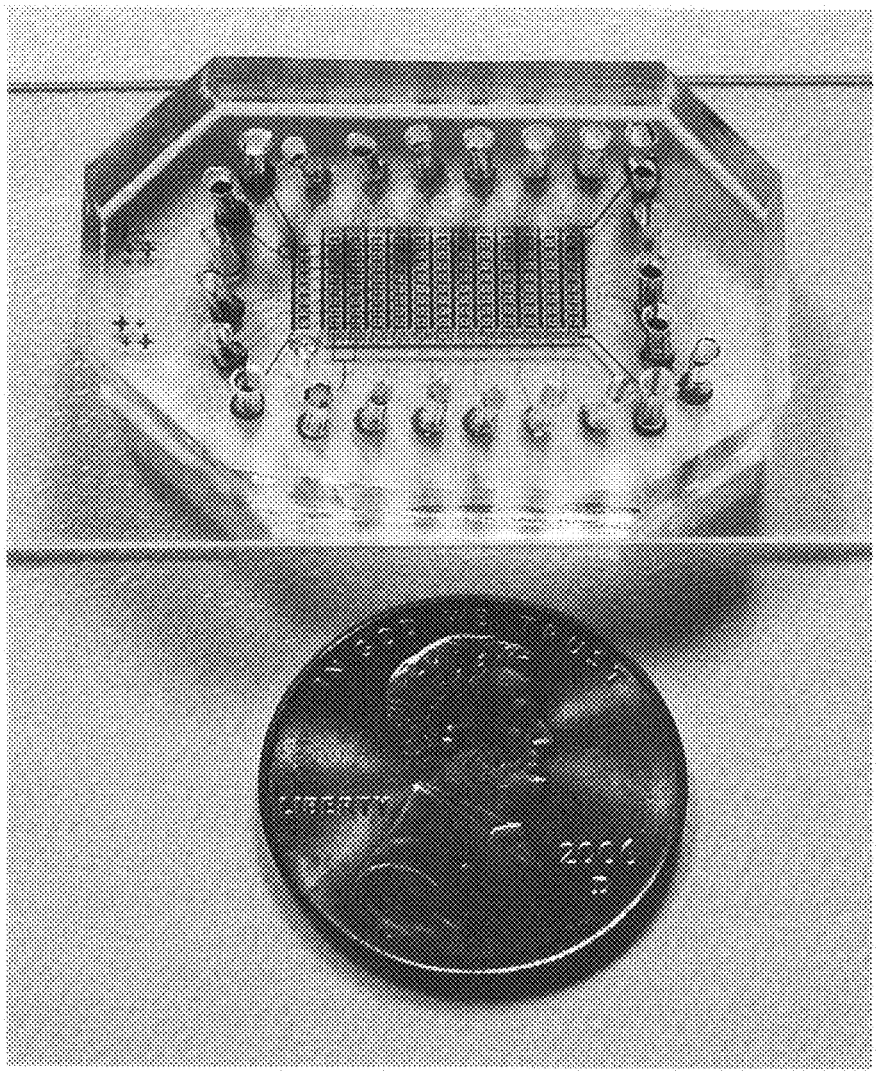
FIG. 1(f) is a digital photograph of a fabricated microfluidic chip in which valves and channels are filled with food colorings for easy visualization.
Figure 1G:
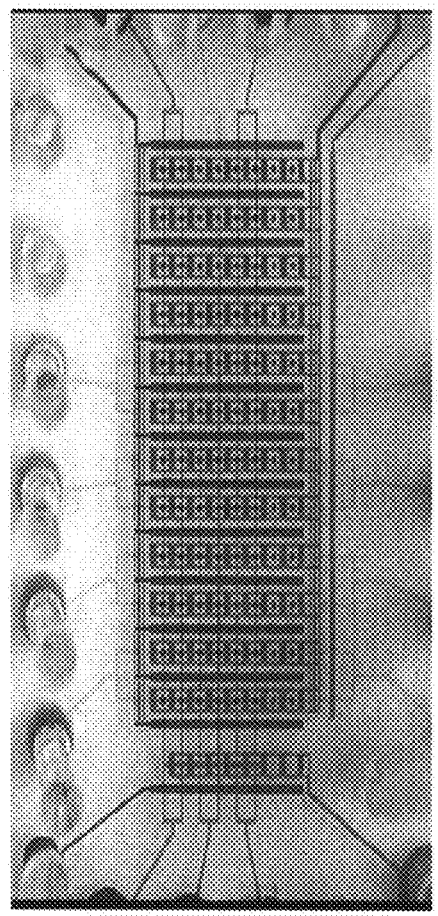
FIG. 1(g) illustrates an enlarged digital photograph of the reaction region of a fabricated microfluidic chip in which valves and channels are filled with food colorings.

FIG. 1(a) illustrates an embodiment of the SPR microscopy system 3 including a microfluidic chip 4 and an SPR imaging system 5. FIGS. 1(b)-1(e) illustrate an embodiment of the microfluidic chip 4 designed for coupling with the SPR imaging system 5. FIG. 1(b) illustrates the layout of the control layer of the microfluidic chip 4. FIG. 1(c) illustrates the layout of the channel layer of the microfluidic chip 4. FIG. 1(d) illustrates the layout of the substrate of the microfluidic chip 4 having a layer of metal spots deposited on certain areas of the substrate. FIG. 1(e) illustrates the layout of the assembled microfluidic chip 4, i.e. FIGS. 1(b)+1(c)+1(d). The valves (red and blue rectangles) in the control layer are aligned onto the channels (light and dark green lines) in the channel layer. Gold spots (brown dots) are located at the intersections of the channels. Two neighboring channels are connected to the same inlet and outlet reservoirs. This design permits four replications of each immunoreaction. FIG. 1(f) is a digital photograph of a fabricated microfluidic chip 4 in which valves and channels are filled with food colorings for easy visualization. FIG. 1(g) illustrates an enlarged digital photograph of the reaction region of a fabricated microfluidic chip 4 in which valves and channels are filled with food colorings.

The upper layer shown in FIG. 1(b), which is called the control layer, is where valves or other flow control components are placed for opening and closing the channels below. The lower layer shown in FIG. 1(c), which is called the channel layer, is where liquid flow occurs. It contains two sets of crossed channels, forming the reaction chambers in the intersections where the metal spots (e.g., gold spot) are located as the platforms for reaction of the first target and the target of interest (e.g., immunoreaction). The design of crossed channels (e.g., in an embodiment the channels do not have to be perpendicular to one another) allows two sets of reagents to be loaded in the reagent reservoirs and sequentially injected. This feature may eliminate one step of reagent loading during the immunoassay, which is beneficial for obtaining real-time SPR images of the microfluidic device. In this particular design embodiment, two neighboring channels are connected to the same inlet and outlet reservoirs. This design permits four replications of each particular reaction. In a particular embodiment, the target of interest is an antibody, so the first target is an antigen of the antibody and is attached to the metal spots. The antibody and antigen are delivered from the reservoirs to the metal spots by liquid flow through the microfluidic channels. The substrate is shown in FIG. 1(d), having a layer of metal spots deposited on certain areas of the substrate.

Both the flow control components and the channels in the microfluidic chip have openings. The openings of the flow control components, namely valve-openings or pump-openings are connected to the pressure manifold to convey actuation pressure. The openings of the channels serve as reservoirs of the liquids to be injected into the channels. When the pressure manifold is used to realize pressure-driven flow in the channels, the reservoirs are also connected to the pressure manifold to convey pressure to the liquids. Usually tubes are used to connect the openings and the pressure manifold.

The channels in the channel layer are about 10 μm to 15 μm in height, about 100 μm to 200 μm in width and about millimeters to centimeters in length. The channel intersections are designed to be circular about 200 μm to 300 μm in diameter. The dimensions of the channels will vary depending on the particular application but are on the order of micrometers to centimeters. The valves and valve-connecting channels in the control layer are about 55 μm in height. The valves are about 200 μm to 300 μm in width and about 500 μm to millimeters in length. The valve-connecting channels are about 30 μm to 150 μm in width and about millimeters to centimeters in length. The dimensions of the valves and valve-connecting channels will vary depending on the particular application but are on the order of micrometers to centimeters. The metal spots are designed to be circular about 127 μm to 250 μm in diameter and about 50 nm in thickness. The diameter of the gold spots will vary depending on the particular application but are on the order of micrometers to millimeters. It is understood that approximately circular metal spots are the preferred embodiment but other shapes and geometries also work well including metal spots with holes.

The microfluidic chip 4 is made of a material such as, but not limited to, polymers, fused silica, silicon, ceramic, titania, alumina, metals, combinations of each, and the like. The polymers can include, but are not limited to, siloxanes (e.g., polydimethylsiloxane (PDMS)), polyimides, polynorbornenes, epoxides, polyarylenes ethers, parylenes, polyolefin (e.g., polypropylene, polyethylene, polymethylpentene), polyetheretherketone, polyimide, fluorocarbon polymers, thermoplastic polymers, combinations thereof, and like polymers. The polymer can be disposed on the appropriate surface using techniques such as, but not limited to, lithography, spin-coating, doctor-blading, sputtering, lamination, screen or stencil-printing, chemical vapor deposition (CVD), or plasma based deposition, and like techniques. Processing steps for forming embodiments of the microfluidic chip 4 are known in the art. The metal spots can be fabricated independently from the microfluidic chip 4 and disposed within the channels of the microfluidic chip 4, or the metal spots can be fabricated as part of the fabrication process of the microfluidic chip 4.

In an embodiment, the microfluidic chip 4 can be fabricated through soft lithography. In an embodiment, the polymer selected is PDMS because of its elasticity, biocompatibility, and easy-to-use microfabrication capability. In an embodiment, the metal spot is a gold film that is integrated into the microfluidic chip 4 for the SPR detection of interfacial reactions. Due to the weak attachment between gold film and PDMS, an array of gold spots (about 127 μm in diameter) is fabricated in order to avoid direct contact with PDMS. Additional details are provided in Example 1.

Figure 2:
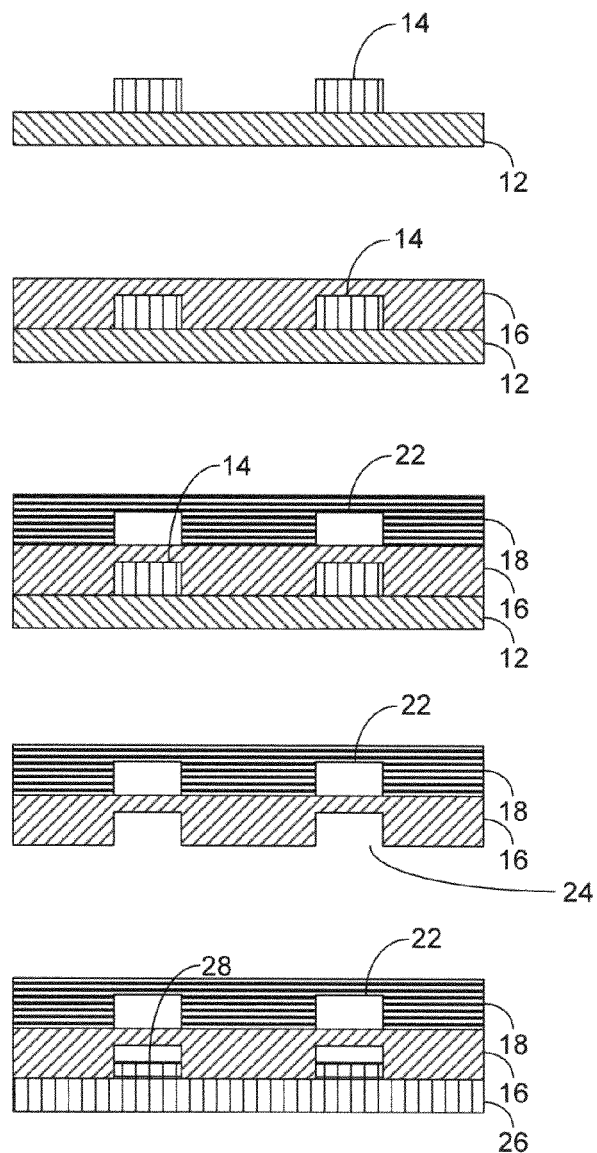
FIG. 2 illustrates a cross-sectional fabrication procedure for producing an embodiment of the microfluidic chip.

An embodiment of the procedure of microfluidic chip fabrication is outlined in FIG. 2 and further discussed in Example 1. In this embodiment, the polymer is PDMS and the metal is gold, however, embodiments are not limited to PDMS and gold. Specifically, the following discussion directed to PDMS and gold is not limited to the use of only PDMS and gold and other polymers and metals can be used, as described herein. A PDMS slab composed of two PDMS layers 16 and 18 and a glass substrate layer 26 having a layer of gold spots 28 deposited are aligned and attached together to form an enclosed network of valves (not shown) and channels 22. The protocol of the microfluidic chip fabrication is shown in Example 1.

In general, a silicon substrate 12 having a photoresist layer 14 disposed on certain areas of the silicon substrate 12 is provided. The photoresist can include, but is not limited to, Shirpley 3612, SPR 220-7, and SU-8, etc. The photoresist patterns are about 100 to 200 μm wide, and are about 10 μm high. The cross-section of the photoresist patterns is reflowed to round shape, while valves (not shown) are included in the microfluidic chip. The dimensions of the photoresist patterns can be varied depending on the end product being produced.

Next, a first PDMS layer 16 is disposed onto the photoresist layer 14 and the silicon substrate 12. The first PDMS layer 16 can be disposed using methods such as, but not limited to, spin-coating PDMS prepolymer, spin-coating dissolved PDMS prepolymer, and the like. The first PDMS layer 16 is about 30 μm to 50 μm high. The dimensions of the first PDMS layer 16 can be varied depending on the end product being produced.

Subsequently, a second PDMS layer 18 is disposed onto the first PDMS layer 16. Valves 22 are formed by disposing the second PDMS layer 18 onto the first PDMS layer 16. The valves 22 are aligned with certain positions of the channels 24 in the first PDMS layer 16 where liquid flow control is needed. The valves 22 are about 55 μm high. The dimensions of the valves 22 can be varied depending on the end product being produced. The second PDMS layer 18 can be disposed using methods such as, but not limited to, dipping-attaching method [H. Wu et al., Lab Chip, 2005, 5, 1393-1398, which is incorporated herein by reference], off-ratio method [D. Guo et al., Langmuir, 2005, 21, 10487-10491, which is incorporated herein by reference], surface-oxidation method [D. C. Duffy et al., Anal. Chem., 1998, 70, 4974-4984, which is incorporated herein by reference], and incomplete-cure method, and the like. The second PDMS layer 18 is about 10 mm high. The dimensions of the second PDMS layer 18 can be varied depending on the end product being produced.

Next, the PDMS slab composed of the first PDMS layer 16 and second PDMS layer 18 is peeled off, or otherwise removed from, the silicon substrate 12 and the photoresist layer 14. The silicon substrate 12 and the photoresist layer 14 can be reused.

Then, a glass substrate 26 (also referred to as a third layer) having a layer of gold spots 28 deposited on certain areas of the glass substrate 26 is provided. The PDMS slab composed of the first PDMS layer 16 and second PDMS layer 18 is disposed onto the glass substrate 26. The PDMS slab is disposed using the dipping-attaching method [H. Wu et al., Lab Chip, 2005, 5, 1393-1398, which is incorporated herein by reference]. The gold spots 28 are aligned with the intersections of the channels 24 (bottom-side open) in the first PDMS layer 16 where the photoresist patterns 14 occupied and are on one side of the channels 24 that define the channels 24. Each gold spot has a height of about 50 nm and a diameter of about 127 μm to 250 μm. In general, the area of each gold spot is close to that of the intersection of channels 24 described herein (see FIGS. 1(b)-1(e) and the corresponding text). The dimensions of the gold spots 28 can be varied depending on the end product being produced.

As described below, a dipping-attaching method is used to seal the PDMS layers (first PDMS layer 16 and second PDMS layer 18) [H. Wu et al., Lab Chip, 5, 1393-1398, 2005, which is incorporated herein by reference]. Based on the dipping-attaching method, a stamping method is used to coat a layer of PDMS on the glass substrate 26 while exposing the gold spots 28. Because the PDMS surface can be passivated by adding D-dodecyl maltoside (DDM) to the sample solutions [B. Huang et al., Lab Chip, 5, 1005-1007, 2005, which is incorporated herein by reference], this stamping method restricts the reactions to happen on the gold spots 24.

Figure 3A:
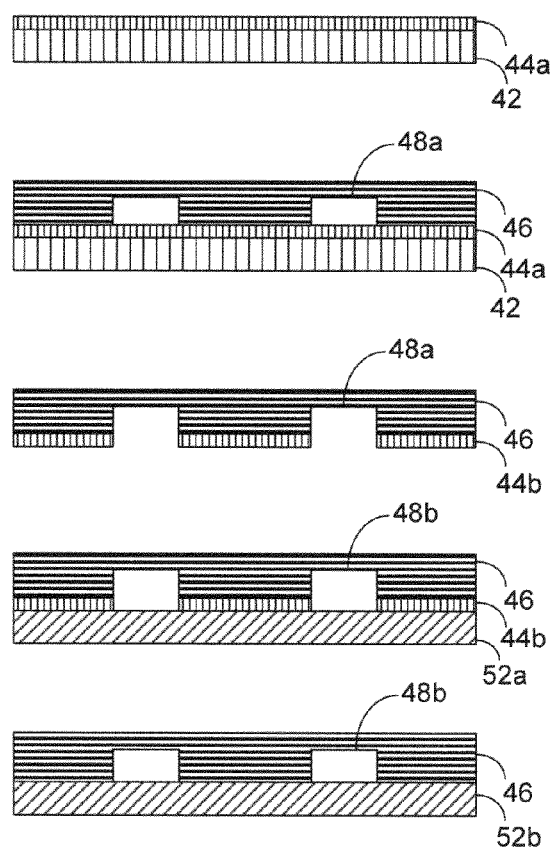
FIG. 3(a) illustrates the dipping-attaching method for attaching components of embodiments of the present disclosure.
Figure 3B:
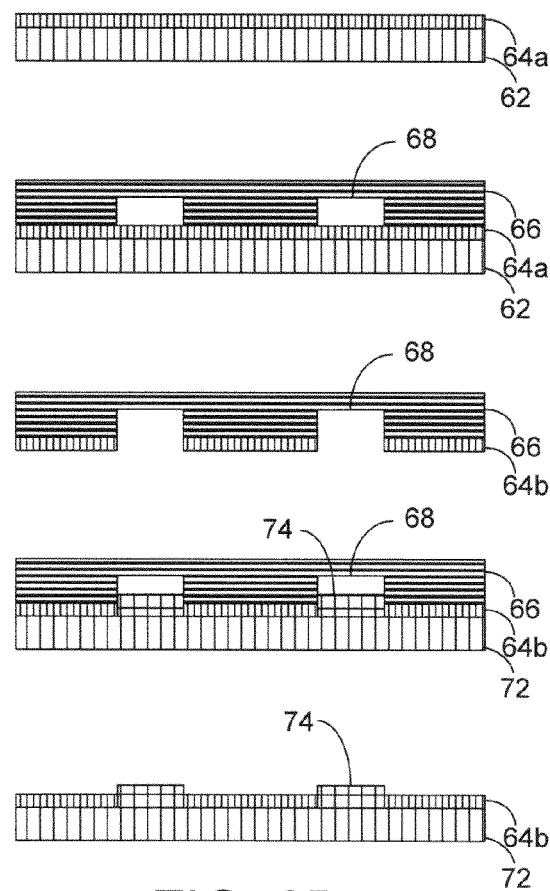
FIG. 3(b) illustrates the stamping method for selectively coating components of embodiments of the present disclosure.

The procedures of the dipping-attaching method and stamping method are schematically shown in FIGS. 3(a) and 3(b), respectively, and discussed in Example 1.

FIG. 3(a) illustrates the dipping-attaching method for attaching components of embodiments of the present disclosure. A glass substrate 42 having a PDMS prepolymer layer 44a disposed thereon is provided. The dimensions of the PDMS prepolymer layer 44a can be varied depending on the end product being produced.

Next, a first PDMS layer 46 is dipped onto the PDMS prepolymer layer 44a. If valves or channels (bottom-side open) are present in the first PDMS layer 46, the inner walls of the valves or channels may not contact with the PDMS prepolymer layer 44a. The dimensions of the first PDMS layer 46 can be varied depending on the end product being produced.

Then, the first PDMS layer 46 is removed from the PDMS prepolymer layer 44a. Subsequently, a PDMS prepolymer layer 44b remains on the first PDMS layer 46.

Next, the first PDMS layer 46 is placed onto a second layer 52. The second layer 52 can be made of PDMS, glass, or combinations thereof. The PDMS prepolymer layer 44b is disposed (sandwiched) between the contact areas of the two layers. The dimensions of the second layer 52 can be varied depending on the end product being produced.

Then, the PDMS prepolymer layer 44b is cured to become a PDMS layer bonded with both the first PDMS layer 46 and the second layer 52 so that the two layers are attached together to become an assembly.

FIG. 3(b) illustrates the stamping method for selectively coating the components of embodiments of the present disclosure. In general, the component to be selectively coated is a glass substrate 72 having a layer of gold spots 74 deposited on certain areas of the glass substrate 72.

A glass substrate 62 having a PDMS prepolymer layer 64a disposed thereon is provided. The dimensions of the PDMS prepolymer layer 64a can be varied depending on the end product being produced.

Next, a PDMS stamp 66 is dipped onto the PDMS prepolymer layer 64a. The PDMS stamp 66 should be designed to have an array of wells 68. The wells or sides 68 avoid contact between PDMS and gold spots 74, while disposing the PDMS stamp 66 onto the glass substrate 62. The inner walls or sides of the wells may not contact with the PDMS prepolymer layer 64a.

Then, the PDMS stamp is removed from the PDMS prepolymer layer 64a. Subsequently, a PDMS prepolymer layer 64b remains on the PDMS stamp 66.

Next, the PDMS stamp 66 is placed onto a second layer 72, which is a glass substrate 72 having a layer of gold spots 74 deposited on certain areas of the glass substrate 72. The wells 68 in the PDMS stamp 66 are aligned with the gold spots 74 so that the gold spots 74 do not contact with the PDMS prepolymer layer 64b. The PDMS prepolymer layer 64b is disposed (sandwiched) between the contact areas of the two layers. The dimensions of the second layer 72 can be varied depending on the end product being produced.

Then the PDMS stamp 66 is removed. Subsequently, a PDMS prepolymer layer 64b remains on the glass substrate 72. The PDMS prepolymer 64c is cured to become a PDMS layer selectively coating the PDMS prepolymer-contacted areas on the glass substrate 72.

As mentioned above, the channels in the channel layer are about 10 μm to 15 μm in height, about 100 μm to 200 μm in width and about millimeters to centimeters in length. The dimensions of the channels will vary depending on the particular application but are on the order of micrometers to centimeters. In an embodiment, the channels are about 100 μm wide and about 10 μm high. Thus, embodiments of the microfluidic chip substantially reduce the volume of reaction chambers from sub-milliliter for standard ELISA to sub-nanoliter in an embodiment of the microfluidic chip. Provided a volume of several microliters of the sample, a typical sample flow velocity of 1 mm/sec can be maintained in the channels for tens of minutes, which prevents the depletion of reactant concentration in reaction chambers and increases the mass transport rate from the bulk phase to the interface. Maintaining a constant sample flow is used for kinetic measurement and accelerates the surface reaction. In contrast, standard ELISA does not replenish the sample. As a result, the reaction time in each step of the immunoassay may be reduced from about 1-2 hours for standard ELISA to about 5-10 minutes. Similar advantages should be realized in other embodiments.

The metal spots can be made of SPR compatible metals. In particular, the metal spots can be made of metals such as, but not limited to, gold, silver, copper, aluminum, alloys of each, and combinations thereof. In an embodiment, the metal spot is made of gold. The metal spot can be about 10 nm to 100 nm thick. The diameter of the metal spot will vary depending on the particular application but are on the order of micrometers to centimeters.

The SPR imaging system can include imaging systems known in the art [B. Rothenhäusler et al., Nature, 1988, 332, 615-617; J. M. Brockman, Annual Review of Physical Chemistry, 2000, 51, 41-63, each of which are incorporated herein by reference], such as the Kretschman's configuration and modifications thereof. In an embodiment of the present disclosure, the SPR imaging system is built based upon a classic Kretschman's configuration.

Figure 4:
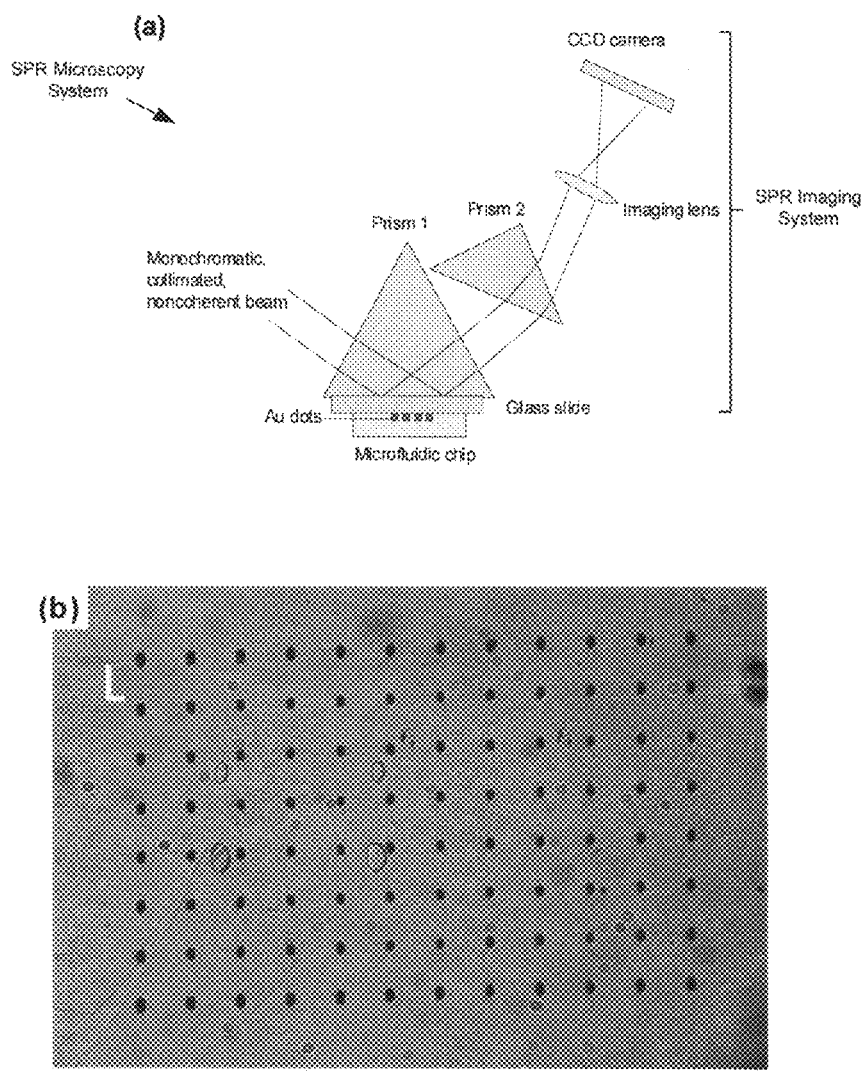
FIG. 4(a) illustrates an optical layout of the double prism geometry for the SPR imaging system.
FIG. 4(b) illustrates a typical SPR image of an array of gold spots integrated in the microfluidic chip (scale bars represent 500 µm in both horizontal and vertical directions).

FIG. 4(a) illustrates an optical layout of the double prism geometry for SPR imaging system, while FIG. 4(b) illustrates a typical SPR image of a gold dot array integrated in the microfluidic chip (scale bars represent 500 μm in both horizontal and vertical directions).

As shown in FIG. 4(a), the sensor surface is illuminated through an equilateral prism (SF10, Schott) by a parallel monochromatic, noncoherent beam generated from a light emitting diode (LED) source, with an angle of incidence at about 60 degrees slightly smaller than the reflectivity minimum. The reflected beam is deflected by a secondary prism, which is used to compensate the tilting between the charge-coupled device (CCD) (e.g., megapixel or more CCD camera) sensor plane and the gold surface plane. Then, an imaging lens is used to send the image to the CCD camera.

In an embodiment, the SPR imaging system operates at near-saturation light intensity to achieve maximum sensitivity. In an embodiment, the SPR imaging system operates so that the incident angle of the impinging light is near the maximum reflectivity dip in order to achieve a maximum signal-to-noise ratio. In an embodiment, the SPR imaging system operates at a double wavelength to achieve maximum sensitivity. In an embodiment, the SPR imaging system includes a light source selected from a coherent light source and an incoherent source light source. A CMOS camera or other digital cameras can be used to receive the image.

FIG. 4(b) illustrates a representative image of a gold dot array integrated in the microfluidic chip. Each gold spot can be observed and can be imaged in focus as a result of the double prism compensation optics [K. Johansen, "Imaging SPR Apparatus," U.S. Pat. No. 6,862,094, issued Mar. 1, 2005, which is incorporated herein by reference], and a homogenous illumination across the whole sensing area free of speckle from a coherent light source.

An embodiment of the present disclosure can be used as a label-free immunoassay. Compared to conventional immunoassays, embodiments of the present disclosure provide a label-free nanoliter-scale immunoassay technology having a number of advantages over previously used systems and methods.

Embodiments of the present disclosure combine a microfluidic chip and SPR imaging to obtain advantages from both miniaturization of the device and label-free detection of biomolecules. The miniaturization results, in low sample consumption and a faster reaction rate in each step of the immunoassay. The label-free detection eliminates the steps for introducing labeling reagents, which substantially simplifies the immunoassay and saves the time.

In addition, embodiments of the present disclosure use a dipping-attaching method to fabricate the microfluidic chip, which provides strong sealing in all attachments during the assembly of the microfluidic chip and prevents leakage between channels. In combination with the DDM coating mentioned above, the stamping method coats the glass surface with PDMS to prevent adsorption in the channels and to restrict reactions to take place on the reaction platforms (location of gold spots).

Furthermore, embodiments of the present disclosure use a double-prism SPR compensation optics and noncoherent LED light source. This configuration improves the SPR image quality, as reflected by the homogenous illumination and sharp features across the whole image (See figures).

EXAMPLES

Now having described the embodiments of the disclosure, in general, the example describes some additional embodiments. While embodiments of the present disclosure are described in connection with the examples and the corresponding text and figures, there is no intent to limit embodiments of the disclosure to these descriptions. On the contrary, the intent is to cover all alternatives, modifications, and equivalents included within the spirit and scope of embodiments of the present disclosure.

Example 1

Protocols of Microfabrication of the Microfluidic Chip (1) Masters for Soft Lithography Photoresist masters for soft lithography are formed on silicon wafers by photolithography. The patterns are designed with computer-aided design software Freehand 10 (Macromedia, San Francisco, Calif.) and printed on transparency films with a high-resolution (3600 dots per inch) printer. To form masters for valves, a 55 µm-thick layer of photoresist SU-8 2035 is spin-coated on a silicon wafer coated with hexamethyldisilizane (HMDS) and soft baked in two steps on a hotplate (65° C. for 3 min and 95° C. for 6 min). After cooling, the photoresist is exposed through a transparency mask and post baked in two steps (65° C. for 1 min and 95° C. for 5 min), and then developed in SU-8 developer. To form a master for the microfluidic channels, a layer of 10 µm-thick photoresist SPR 220-7 is spin-coated on a silicon wafer and baked on a hotplate (95° C. for 200 s). The photoresist is exposed through a transparency mask and developed. The wafer was then baked in an oven (110° C. for 1 h) to reflow the photoresist to form rounded features. The master surface is silanized by exposure to methyltrichlorosilane vapor in a desiccator for 30 min, in order to prevent adhesion of PDMS to the master during the PDMS curing process.

(2) Assembly of Microfluidic Chips

PDMS slabs are formed and sealed by multilayer soft lithography. The valve slab is formed by casting PDMS prepolymer (RTV 615 A:B with a mass ratio of 10:1) against a valve master and curing the PDMS in an oven (80° C. for about 2 h). The valve slab (about 1 cm thick) is then peeled from the master and holes are punched for connection to an external pressure controller. The channel slab is formed by spin-coating (2.0 krpm for 60 s) PDMS prepolymer on a channel master and curing the PDMS in an oven (80° C. for about 30 min). The valve slab is aligned and attached to the channel slab under a stereo microscope. The attachment is carried out by dipping the valve slab on a thin layer of PDMS prepolymer (TLPP), which is formed by spin-coating PDMS prepolymer cyclohexane solution at 3.0 krpm for 30 s on a glass slide, and then affixing on the channel slab. The glue layer of PDMS prepolymer between the affixed PDMS slabs is further cured (80° C. for about 1 h) to complete the attachment. The assembly of PDMS slabs is peeled from the channel master and holes are punched as reservoirs. A supporting layer of PDMS is formed on a glass substrate deposited with thin gold spots by first dipping a PDMS stamp on a TLPP and secondly stamping on the glass substrate to leave a certain thickness of PDMS prepolymer, ensuring the gold membranes are facing to the wells on the stamp. The supporting layer is cured at 80° C. for about 30 min. The assembly of PDMS slabs is aligned and attached to the supporting layer of PDMS by dipping it on a TLPP and then affixing on the supporting layer of PDMS to form a microfluidic chip. The glue layer of PDMS prepolymer is further cured (80° C. for about 1 h) to complete the attachment and finish the assembly of the microfluidic chip.

Example 2

Results of Label-Free Immunoassay in Microfluidic Chip

Biotin and anti-biotin antibody are chosen as the immunoreaction pair used in the present embodiment. Referring to the microfluidic chip design shown in FIG. 1(a), the vertical channels are first filled with different mixtures of biotinylated bovine serum albumin (BSA) and native BSA in different ratios. In about 30 minutes of incubation time, both BSAs are physically adsorbed onto the gold spots. This procedure creates a series of spots having different biotin densities between the vertical lines. After thoroughly rinsing the vertical channels with PBS (phosphate-buffered saline), the horizontal channels are filled with different concentrations of anti-biotin antibody solution, each containing 0.1% w/v DDM to prevent physisorption of the antibody to the PDMS surface. The antibody binding to the adsorbed biotinylated BSA is monitored by SPR imaging as a function of time.

Figure 5A:
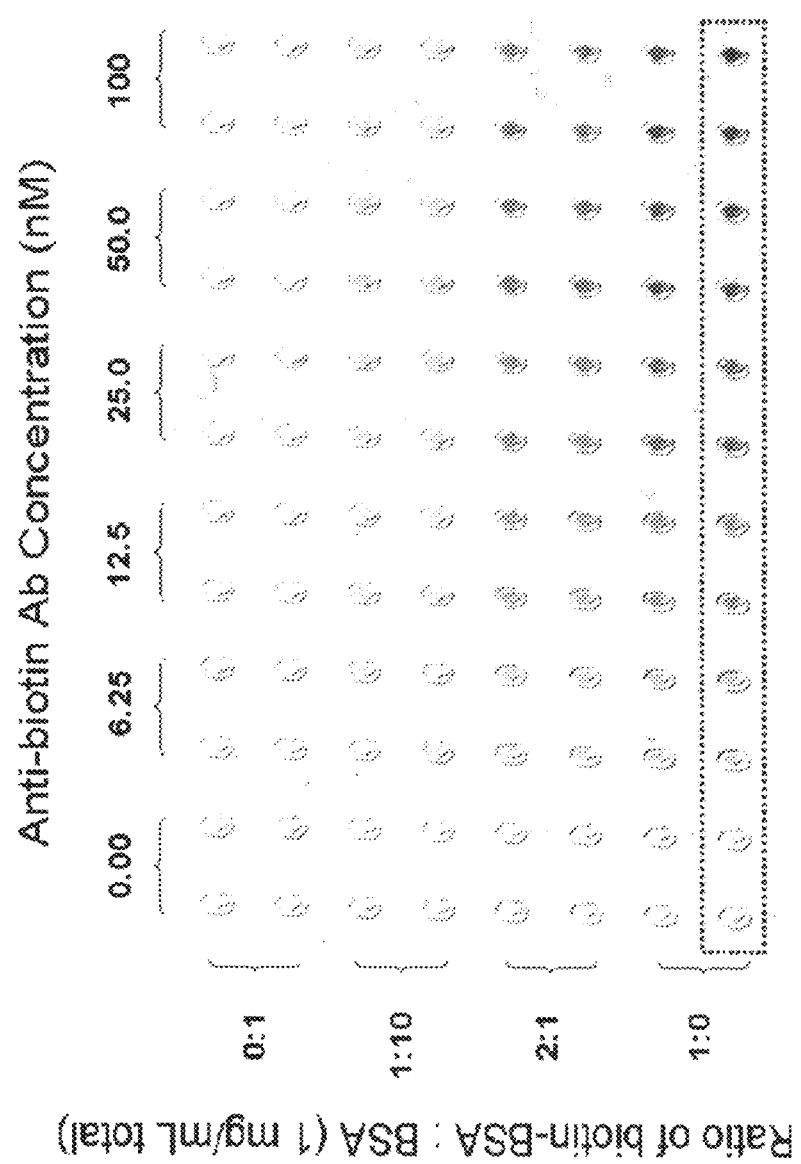
FIG. 5(a) illustrates the background corrected SPR image obtained after anti-biotin antibody binding to biotinylated BSA attached to the gold spots. The vertical lines represent different mixtures of biotinylated BSA and native BSA with a total concentration of 1 mg/mL. The horizontal lines represent different anti-biotin antibody concentrations.

FIG. 5(a) illustrates the background corrected SPR image obtained after anti-biotin antibody binding to biotinylated BSA attached to the gold spots. The vertical lines represent different mixtures of biotinylated BSA and native BSA with a total concentration of 1 mg/mL. The horizontal lines represent different anti-biotin antibody concentrations.

Figure 5B:
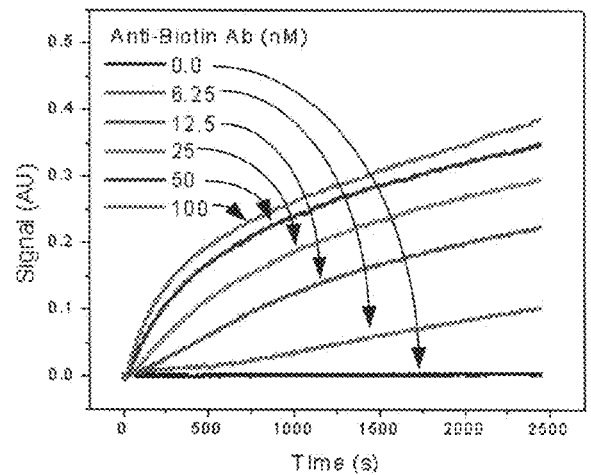
FIG. 5(b) illustrates the kinetic curves of anti-biotin antibody binding to pure biotinylated BSA-attached gold spots, as indicated by the dotted box in FIG. 5(a). Every two gold spots with replicated immunoreactions are averaged.

FIG. 5(b) illustrates the kinetic curves of anti-biotin antibody binding to pure biotinylated BSA-attached gold spots, as indicated by the dotted box in FIG. 5(a). Every two gold spots with replicated immunoreactions are averaged. From the kinetic curves it is found that the SPR signals are easily distinguishable at about 10 min, indicating the capability of fast sample quantitation. Within about 40 min, the SPR signal shows biphasic kinetics of immunoreactions and is still yet to reach equilibrium. Therefore, calibration curves are needed in quantitation experiments to eliminate the influence of experiment-to-experiment variations.

Example 3

Dose-Response Curves

Figure 6:
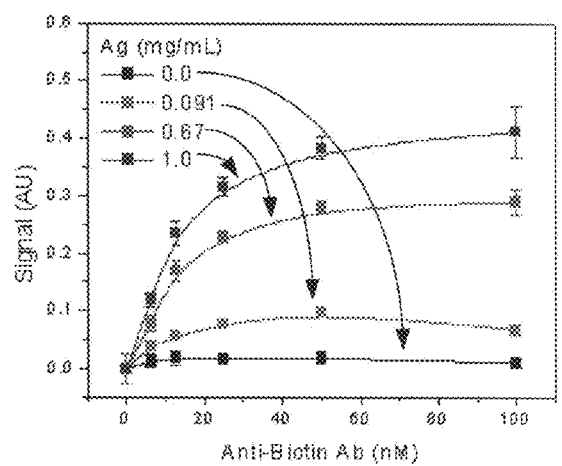
FIG. 6 illustrates the dose-response curves obtained by averaging the results of replicated immunoreactions on every four gold spots.

FIG. 6 illustrates the dose-response curves obtained by averaging the replicated immunoreaction results on every four gold spots. Each dose-response curve reaches saturation at a certain concentration of anti-biotin Ab, which may be explained by the limited binding capacity of biotinylated BSA immobilized on the gold spots. The uncertainty associated with each point is the standard, deviation of the four replicated immunoreactions.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include ±1%, ±2%, ±3%, ±4%, ±5%, ±6%, ±7%, ±8%, ±9%, or ±10%, or more of the numerical value(s) being modified. In addition, the phrase "about 'x' to 'y'" includes "about 'x' to about 'y'".

It should be emphasized that the above-described embodiments of the present disclosure are merely possible examples of implementations, and are merely set forth for a clear understanding of the principles of this disclosure. Many variations and modifications may be made to the above-described embodiment(s) of the disclosure without departing substantially from the spirit and principles of the disclosure. All such modifications and variations are intended to be included herein within the scope of this disclosure and protected by the following claims.

We claim:

1. A surface plasmon resonance (SPR) microscopy system comprising:
    an integrated microfluidic chip that includes a plurality of layers, wherein the microfluidic chip includes at least a first layer and a second layer, wherein the first layer includes a plurality of microfluidic channels, wherein the second layer includes one or more flow control components, wherein an array of metal spots is disposed on a side of the channels in the first layer, and
    an SPR imaging system, wherein the SPR imaging system is adapted to detect an SPR signal associated with each metal spot, and
    a pressure manifold to actuate flow control components in the second layer of the microfluidic chip and to realize pressure-driven flow of liquids in the channels in the first layer of the microfluidic chip,
    wherein the plurality of microfluidic channels in the first layer of the microfluidic chip includes a first set of channels and a second set of channels, wherein the first set of channels and the second set of channels are in communication at a position where a channel of the first set of channels and a channel of the second set of channels intersect one another, and wherein a metal spot of the array of the metal spots is located at the position where the first set of channels and the second set of channels perpendicularly intersect one another.

2. The SPR microscopy system of claim 1, wherein the flow control components are selected from a valve and a pump.

3. The SPR microscopy system of claim 1, wherein the microfluidic chip has openings of both the flow control components in the second layer and the channels in the first layer, wherein the openings of the flow control components are connected to the pressure manifold to convey actuation pressure, wherein the openings of the channels serve as reservoirs of the liquids to be injected into the channels, wherein when the pressure manifold is used to realize pressure-driven flow in the channels, the reservoirs are also connected to the pressure manifold to convey pressure to the liquids.

4. The SPR microscopy system of claim 1, wherein the pressure control manifold controls the pressure-driven flow of liquids to the metal spots to allow binding and washing.

5. The SPR microscopy system of claim 1, wherein the pressure-driven flow is realized by an additional device is selected from peristaltic pumps, piston pumps, and combinations thereof.

6. The SPR microscopy system of claim 1, wherein the flow control components in the second layer of the microfluidic chip include valves capable of blocking the channels in the first layer, wherein the first and the second set of channels are alternatively blocked via a gate so that only one of the first and the second set of channels allows flow of liquids at a time.

7. The SPR microscopy system of claim 1, wherein the number of metal spots is up to 1024.

8. A method of the label-free detection of a first target/second target pair comprising:
    providing the surface plasmon resonance (SPR) microscopy system, wherein the SPR microscopy system includes:
    an integrated microfluidic chip that includes a plurality of layers, wherein the microfluidic chip includes a first layer and a second layer, wherein a first layer includes a plurality of microfluidic channels, wherein a second layer includes one or more flow control components, wherein an array of metal spots is disposed on a side of the channels in the first layer, wherein the plurality of microfluidic channels in the first layer of the microfluidic chip includes a first set of channels and a second set of channels, wherein the first set of channels and the second set of channels are in communication at a position where a channel of the first set of channels and a channel of the second set of channels intersect one another, and wherein a metal spot of the array of the metal spots is located at the position where the first set of channels and the second set of channels intersect one another, and
    an SPR imaging system, wherein the SPR imaging system is adapted to detect an SPR signal associated with each metal spot;
    exposing the array of metal spots to a sample including a second target, wherein the first target and the second target interact to form a first target/second target pair; and detecting an SPR signal associated with each metal spot, wherein detection of the SPR signal is correlated to the presence or absence of the first target/second target pair.

9. The method of claim 8, further comprising:
delivering the first target to the metal spot using a first channel using the flow control system; and
delivering the second target to the metal spot using a second channel using the flow control system.

10. The method of claim 8, further comprising:
rinsing the first channel and the metal spot to remove unbound first targets prior to delivering the second target.

11. The method of claim 8, further comprising:
detecting a first SPR signal associated with each metal spot when the first target is bound to the metal spot;
rinsing the first channel and the metal spot to remove unbound first targets;
exposing the array of metal spots to a sample including a second target;
rinsing the second channel and the metal spot to remove unbound second targets; and
detecting a second SPR signal associated with each metal spot; wherein the first SPR signal and the second SPR signal are detectably different if the first target/second target pair is present on the metal spot.

12. The method of claim 8, wherein detecting a SPR signal includes detecting real time SPR images.

13. The method of claim 8, wherein the first target and the second target are selected from a chemical target or a biological target.

14. The method of claim 8, wherein the first target and the second target are selected from: halogenated hydrocarbons, aromatic hydrocarbons, volatile organic compounds, surfactants, polycyclic aromatic hydrocarbons (PAHs), pesticides, macromolecules, pathogens, toxins, nerve agents, chemical/biochemical/biological warfare agents, or combinations thereof.

15. The method of claim 8, wherein the first target and the second target are selected from: deoxyribonucleic acid (DNA), ribonucleic acid (RNA), nucleotides, oligonucleotides, nucleosides, polynucleotides, proteins, peptides, polypeptides, selenoproteins, antibodies, antigens, protein complexes, aptamers, lipids, fatty acids, glycoproteins, carbohydrates, fatty acids, fatty esters, macromolecular polypeptide complexes, vitamins, co-factors, whole cells, eukaryotic cells, prokaryotic cells, micelles, viruses, bacteria, protozoa, archaea, fungi, algae, spores, apicomplexan, trematodes, nematodes, mycoplasma, or combinations thereof.

16. The method of claim 8, wherein one of the first target and the second target is an antigen and the other of the first target and the second target is an antibody.

* * * * *